(12) United States Patent
Rao

(10) Patent No.: US 12,251,163 B2
(45) Date of Patent: Mar. 18, 2025

(54) ARTIFICIAL INTELLIGENCE BASED VASCULAR MAPPING AND INTERVENTIONAL PROCEDURE ASSISTING PLATFORM BASED UPON DYNAMIC FLOW BASED IMAGING AND BIOMARKERS

(71) Applicant: SCA Robotics, Moraga, CA (US)

(72) Inventor: Rob K. Rao, Moraga, CA (US)

(73) Assignee: SCA ROBOTICS, Moraga, CA (US)

( * ) Notice: Subject to any disclaimer, the term of this patent is extended or adjusted under 35 U.S.C. 154(b) by 735 days.

(21) Appl. No.: 17/308,009

(22) Filed: May 4, 2021

(65) Prior Publication Data

US 2021/0338330 A1     Nov. 4, 2021

Related U.S. Application Data

(60) Provisional application No. 63/019,712, filed on May 4, 2020.

(51) Int. Cl.
*A61B 34/10* (2016.01)
*A61B 34/20* (2016.01)
*G06T 7/00* (2017.01)

(52) U.S. Cl.
CPC .............. *A61B 34/10* (2016.02); *A61B 34/20* (2016.02); *G06T 7/0012* (2013.01);
(Continued)

(58) Field of Classification Search
CPC ... A61B 34/10; A61B 34/20; A61B 2034/104; A61B 2034/105; A61B 2034/107; A61B 2034/2046; A61B 2034/108; A61B 2034/256; A61B 2090/3933; G06T 7/0012; G06T 2207/30101; G16H 30/40;
(Continued)

(56) References Cited

U.S. PATENT DOCUMENTS 10,327,929 B2 *   6/2019   Syed ................ A61B 17/00
10,668,258 B1 *   6/2020   Calhoun ............ A61M 29/02
(Continued)

OTHER PUBLICATIONS

Poplin et al, Prediction of cardiovascular risk factors from retinal fundus photographs via deep learning, Nature Biomedical Engineering 2, pp. 158-164(2018).
Liang Shen, MSc et al, 2. Rapid Automated Quantification of Cerebral Leukoaraiosis on CT Images: A Multicenter Validation Study, Radiology, 2018.
Morton Kern, MD, 3. Angiographic Projections Made Simple: An Easy Guide to Understanding Oblique Views CathLab Digest, vol. 19—Issue 8—Aug. 2011.
(Continued)

*Primary Examiner* — Santiago Garcia
(74) *Attorney, Agent, or Firm* — Blynn L. Shideler; Krisanne Shideler; BLK Law Group

(57) ABSTRACT

An artificial intelligence based vascular mapping and interventional procedure assisting platform configured to identify at least the femoral artery and the bifurcation point of the femoral artery of a patient based upon dynamic imaging of the patient. The platform may be a stroke management tool in which an angiogram and conventional bloodwork can be inputted into the platform and the platform provides one of i) classification of a stroke and stroke prediction; and whether an interventional procedure is indicated and wherein if interventional procedure is indicated then vascular mapping is provided with bifurcation points and the desired access illustrated together with a listing of accepted or counter indicated closure systems that may be used.

14 Claims, 1 Drawing Sheet

(52) U.S. Cl.
CPC ... *A61B 2034/104* (2016.02); *A61B 2034/105* (2016.02); *A61B 2034/107* (2016.02); *A61B 2034/2046* (2016.02); *G06T 2207/30101* (2013.01)

(58) Field of Classification Search
CPC ........ G16H 40/20; G16H 50/20; G16H 50/30; G16H 20/40
See application file for complete search history.

(56) References Cited

U.S. PATENT DOCUMENTS

| | | | | |
|---|---|---|---|---|
| 2009/0182268 | A1* | 7/2009 | Thielen | A61M 25/0138 604/95.04 |
| 2011/0257545 | A1* | 10/2011 | Suri | A61B 8/5223 600/508 |
| 2012/0029436 | A1* | 2/2012 | Yassinzadeh | A61B 17/12136 606/213 |
| 2012/0220875 | A1* | 8/2012 | Suri | G16H 70/60 600/407 |
| 2015/0174379 | A1* | 6/2015 | Bagaoisan | A61M 25/10 604/102.03 |
| 2019/0117087 | A1* | 4/2019 | Yasunaga | A61B 5/7221 |
| 2019/0246904 | A1* | 8/2019 | Kim | A61B 5/7425 |
| 2019/0255286 | A1* | 8/2019 | Syed | A61M 25/0108 |
| 2020/0310098 | A1* | 10/2020 | Ince | G06T 7/0012 |
| 2021/0321880 | A1* | 10/2021 | Bobo | A61B 5/026 |
| 2021/0390689 | A1* | 12/2021 | Buckler | G06T 7/0012 |
| 2021/0393333 | A1* | 12/2021 | Sganga | G16H 30/40 |
| 2022/0012877 | A1* | 1/2022 | Buckler | G06T 7/0012 |
| 2022/0151580 | A1* | 5/2022 | Itu | G06T 7/0012 |
| 2022/0265241 | A1* | 8/2022 | Wodlinger | A61B 8/461 |
| 2023/0065014 | A1* | 3/2023 | Yu | A61K 31/19 |

OTHER PUBLICATIONS

Muhammad N. Mengal et al, Assessment of Femoral Artery Bifurcation Level with Conventional Angiography Cureus 10(10): e3479 (Oct. 22, 2018.
Cignoni, P.; Rocchini, C; Scopigno, R., Metro: Measuring Error on Simplified Surfaces. Computer Graphics Forum 17 (2): 167-174 (1998).
Peter M. Rothwell, et al., Equivalence of measurements of carotid stenosis. A comparison of three methods on 1001 angiograms. European Carotid Surgery Trialists' Collaborative Group Stroke 25:2435-2439 (1994).
Melisa Piper Hunter et al, Detection of microRNA expression in human peripheral blood microvesicles PLoS One. 2008;3(11):e3694.
Meng Li, Junping Zhang, Circulating microRNAs: potential and emerging biomarkers for diagnosis of cardiovascular and cerebrovascular diseases Biomed Res Int. 2015; 2015:730535.
Johan Skog, Glioblastoma microvesicles transport RNA and proteins that promote tumour growth and provide diagnostic biomarkers, Nat Cell Biol. 2008;10(12):1470-1476.
Olga Vaksman et al, Exosome-derived miRNAs and ovarian carcinoma progression, Carcinogenesis. 2014;35(9):2113-2120.
Brittany Dewdney, MSc, et al, Circulating microRNAs as biomarkers for acute ischemic stroke: a systematic review, J Stroke Cerebrovasc Dis. 2018;27(3):522-530.
Ceren Eyileten et al, MicroRNAs as diagnostic and prognostic biomarkers in ischemic Stroke—A comprehensive review and bioinformatic analysis, Cells. 2018;7(12):249.
Da-Zhi Liu, Brain and blood microRNA expression profiling of ischemic stroke, intracerebral hemorrhage, and kainate seizures, J Cereb Blood Flow Metab. 2010; 30(1):92-101.
M. Yashar et al, Extracellular microRNAs in blood differentiate between ischaemic and haemorrhagic stroke subtypes J Extracell Vesicles. 2020; 9(1): 1713540.

* cited by examiner

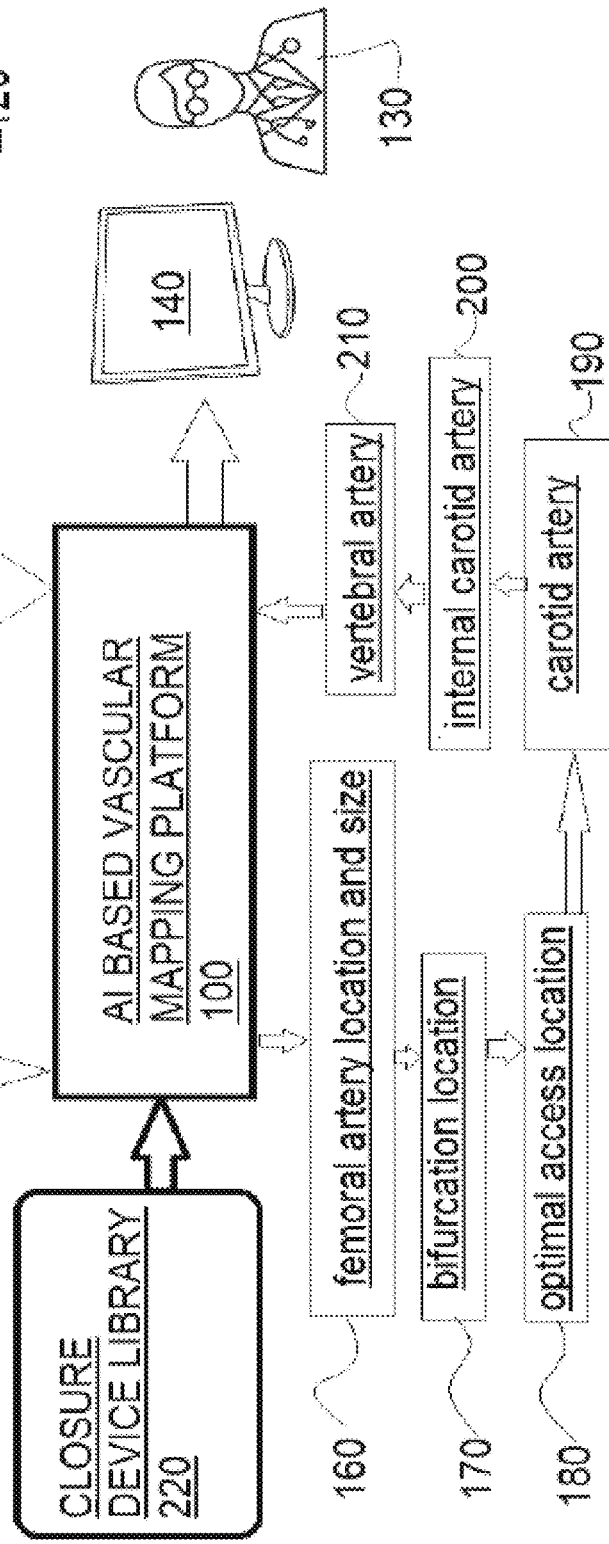

ARTIFICIAL INTELLIGENCE BASED VASCULAR MAPPING AND INTERVENTIONAL PROCEDURE ASSISTING PLATFORM BASED UPON DYNAMIC FLOW BASED IMAGING AND BIOMARKERS

RELATED APPLICATIONS

The present application claims the benefit of U.S. Provisional Patent Application Ser. No. 63/019,712 Filed May 4, 2020 titled "Artificial Intelligence Based Vascular Mapping and Interventional Procedure Assisting Platform Based Upon Dynamic Flow Based Imaging and Biomarkers" which is incorporated herein by reference.

BACKGROUND OF THE INVENTION

1. Field of the Invention

The present invention relates to an artificial intelligence based vascular mapping and interventional procedure assisting platform which may form, in one embodiment a stroke assist tool.

2. Background Information

Artificial intelligence is incredible tool being used across numerous systems. For example, August 2018, a workshop was held at the National Institutes of Health (NIH) in Bethesda, Md., to explore the future of artificial intelligence (AI) in medical imaging. The workshop was co-sponsored by NIH, Radiological Society of North America (RSNA), American College of Radiology (ACR) and the Academy for Radiology and Biomedical Imaging Research (The Academy), who aimed to foster collaboration in applications for diagnostic medical imaging, identify knowledge gaps and develop a roadmap to prioritize research needs. The group's research roadmap was published as a special report in the journal Radiology on Apr. 16, 2019. In addition to establishing image labeling and annotation methods for facilitating model development in the field, the report restated the need for the development of novel pre-trained model architectures, tailored for clinical imaging data, along with methods for distributed training that reduce the need for data exchange between institutions.

With its increasing role in medical imaging, artificial intelligence (AI) gradually is becoming a go-to technology for building custom healthcare software to diagnose and facilitate treatment of a wide range of diseases, from diabetic retinopathy to skin cancer. With several vendors now working on stroke detection AI algorithms and a few of these gaining U.S. Food and Drug Administration (FDA) approval, stroke may be the next frontier to conquer.

According to Centers for Disease Control and Prevention (CDC), stroke puts a significant burden on the U.S. healthcare, being one of the leading causes of long-term disability and accounting for $34 billion in yearly costs for care delivery, medications, and missed work days. Indeed, a major part of the expenditures related to stroke arises from a lengthy rehabilitation period. For most acute conditions, discharge from the hospital means that the patient has almost or completely recovered. But when it comes to stroke, discharge is just the beginning of a journey towards recovery.

Obviously the best case would be to prevent patients from having a stroke, or, at least, accelerate time-to-diagnosis and thus minimize the brain damage. If a stroke is diagnosed immediately, the patient may fully regain their mobility, self-care and social skills, progress sooner, or experience only a slight decline But an inaccurate diagnosis may lead to dire consequences. Ischemic stroke is the most common type of this condition, and it is usually treated with tissue plasminogen activator (tPA) to dissolve the blood clots and restore the blood flow to the brain. However, this medication can be deadly to a patient with a hemorrhagic stroke, because it will increase the internal bleeding. In turn, a hemorrhagic stroke may require surgical intervention or coil insertion to stop the bleeding. Deciding on the stroke type can be challenging, but health specialists still need to figure it out quickly to save the patient's life and functionality.

The current maturity level of artificial intelligence technology can unlock numerous opportunities for stroke care, from uncovering the underlying risks to develop stroke in certain patient groups to alerting health specialists about suspicious abnormalities on medical scans during triage.

CDC also notes that stroke is preventable in up to 80 percent of cases, if the patients recognize and mitigate the risks in due time. However, most health risks are related to a patient's habits and choices in nutrition, physical activity, and lifestyle. Therefore, a patient might tend to disregard their physician's suggestions. A study from Google's AI team, *Prediction of cardiovascular risk factors from retinal fundus photographs via deep learning*, Nature Biomedical Engineering 2, pages 158-164(2018), attempts to throw abstractions away and show the patients their future by analyzing retinal images, extracting their personal health risks, and making predictions based on the knowledge received. Their system can extract a range of risk factors critical for the occurrence of cardiovascular disease and stroke, such as body mass index (BMI), hemoglobin A1c (HbA1c), systolic and diastolic blood pressure, as well as smoking status. The researchers reported their algorithms succeeded in predicting the chances of particular patients developing stroke or heart attack in a five-year period with a 70 percent accuracy.

Another UK Research study, Rapid Automated Quantification of Cerebral Leukoaraiosis on CT Images: A Multicenter Validation Study *Radiology,* 2018, concentrated on analyzing CT and MRI scans to detect and grade the small vessel disease (SVD). This is a neurological condition that hinders the blood supply of the brain, causing stroke and dementia. While it can be diagnosed via CT and MRI scans without the bias or risk to confuse it with a mimicking condition, the precise SVD's severity evaluation is rather complex. In the meantime, health specialists need to grade the disorder as accurate as possible. For example, if a patient has an ischemic stroke while having severe SVD, the administration of tPA can lead to a brain hemorrhage, increasing the damage to patient health. The researchers claim that their algorithm was able to achieve an 85 percent accuracy in estimating the SVD severity from CT and MRI scans.

AI's "superpower" also helps define the stroke type shortly after the onset, detecting the slightest deviations on the CT and MRI scans. Machine learning algorithms can distinguish an ischemic stroke from a hemorrhagic or other types and also reduce the possibility to overlook other conditions, such as meningitis, seizure, encephalitis, acute demyelination, abscess and subdural hematoma. In early 2018, the FDA approved an AI algorithm for use in a clinical decision support system for triage. Called VIZ.AI CONTACT, it can analyze CT scans and detect stroke signs in medical images, making a preliminary diagnosis. If the system suspects a stroke in a particular patient, it notifies a neurovascular specialist about the findings via a smartphone or a tablet. The specialist's attention will be refocused to the most acute cases, while the radiologist can proceed with reviewing less urgent scans. This AI-enabled process optimization can ensure timely care for patients who may not be able to pull through the standard review procedure without risking their health or even life.

Surviving a stroke is only a starting point of the patient's fight for their full and independent life. The sooner a person receives adequate medical care, the more they can achieve during the rehabilitation, hopefully up to regaining their mobility and social skills completely.

Adding to the above mix of technologies and related issues, the COVID-19 pandemic has changed hospital economics. Providers are forced to limit elective procedures and patients are foregoing care even for emergencies as they are afraid to come to the hospital. This has left health systems with uncertainty, trying to find ways to continue providing cost effective, high quality care during an unprecedented pandemic that has made coordinating patient care that much more difficult. Ai systems properly implemented can play a critical role coordinating care during this crisis; reducing time to treatment, improving outcomes, increasing access to care and helping the healthcare system recover economically. AI platforms can help coordinate care through optimizing workflows, and helping transfer the right patients, increasing mechanical thrombectomy rates and reducing lengths of stay.

There remains a need for Artificial intelligence to support health specialists and provide them with actionable insights to accelerate diagnosis and ensure accurate medication and intervention decisions in the shortest possible time after the stroke onset. Proper AI platforms can even help reduce the risk of developing the condition in some patients, eliciting subtle warning patterns and alerting the clinicians about the upcoming crisis.

SUMMARY OF THE INVENTION

It is an object of the present invention to provide an artificial intelligence based vascular mapping and interventional procedure assisting platform based upon dynamic flow based imaging, such as angiograms, and biomarkers. One aspect or application of the present invention is as a stroke assessment and management tool.

One aspect of the invention provides an artificial intelligence based vascular mapping and interventional procedure assisting platform configured to identify at least the femoral artery and the bifurcation point of the femoral artery of a patient based upon dynamic imaging of the patient.

One aspect of the invention provides an artificial intelligence based vascular mapping and interventional procedure assisting platform wherein the platform is coupled to a closure device library having a complete listing of available closures as well as appropriate indications of use and contra-indications of use and wherein the platform incorporates the patient physiology based upon dynamic imaging of the patient together with the library to designate which closure devices would be appropriate and which closure devices would be contra-indicated.

One aspect of the invention provides an artificial intelligence based vascular mapping and interventional procedure assisting platform wherein the platform is a stroke management tool in which an angiogram and conventional bloodwork can be inputted into the platform and the platform provides one of i) classification of a stroke and stroke prediction; and whether an interventional procedure is indicated and wherein if interventional procedure is indicated then vascular mapping is provided with bifurcation points and the desired access illustrated together with a listing of accepted or counter indicated closure systems that may be used.

These and other advantages of the present invention will be clarified in the brief description of the preferred embodiment taken together with the drawings in which like reference numerals represent like elements throughout.

DESCRIPTION OF THE FIGURE

FIG. 1 is a schematic representation of an artificial intelligence based vascular mapping and interventional procedure assisting platform according to one embodiment of the invention.

DESCRIPTION OF THE PREFERRED EMBODIMENTS

The present invention provides effective and efficient precision artificial intelligence based vascular mapping and interventional procedure assisting platform 100 based upon dynamic flow based imaging 110 and biomarkers, namely blood based biomarkers 120. One specific application of the present invention is as a stroke assessment and management tool or platform.

Artificial intelligence (AI) generally concerns the development of platforms and associated methods that enable computers to behave in ways generally considered "intelligent" when those same behaviors are exhibited by humans. AI is the most general term to define this field of inquiry and is broadly understood by scientists and lay public. For the foreseeable future, AI systems will be narrow, typically constructed to assist humans with a specific task, such as driving a car, targeting an advertisement, or interpreting a mammogram. The AI platform of the present invention is narrowly configured as a vascular mapping and interventional procedure assisting platform based upon dynamic flow based imaging and biomarkers as detailed below. One purpose of AI platform of the invention is to create a tool that improves patient outcomes. The AI platform 100 of the invention, in one aspect, takes the form of imaging decision support system or platform 100 that provides actionable advice that can be viewed on a display 140 to imaging professionals 130.

Artificial intelligence (AI) actually has several working definitions and can be efficiently defined herein as the simulation of human intelligence processes by machines, especially computer systems. These processes include learning (the acquisition of information and rules for using the information), reasoning (using rules to reach approximate or definite conclusions) and self-correction. Machine learning is a subset of AI, and can be categorized by its ability to modify itself when exposed to more data; i.e. machine learning is dynamic and does not require human intervention to make certain changes. Deep learning is a subset of machine learning, and herein it is referring to deep artificial neural networks.

Artificial neural networks are a set of algorithms, modeled loosely after the human brain, that are designed to recognize patterns. Artificial neural networks interpret sensory data through a kind of machine perception, labeling or clustering raw input. The patterns they recognize are numerical, contained in vectors, into which all real-world data, be it images, sound, text or time series, must be translated.

Artificial neural networks generally help cluster and classify and can be thought of generally as a clustering and classification layer on top of the data that is stored and managed. Generally, artificial neural networks, such as the platform of the present invention, help to group unlabeled data according to similarities among the example inputs, and they classify data when they have a dataset to train upon. Artificial neural networks can also extract features that are fed to other algorithms for clustering and classification; so deep neural networks may be considered as components of larger machine-learning applications involving algorithms for reinforcement learning, classification and regression.

Interventional Medicine and Interventional Medical Practitioners 130

Interventional medical practitioners 130 are specialists who do minimally invasive procedures instead of surgery or other treatment. Traditionally, these procedures utilize various imaging and catheterization techniques in order to diagnose and treat vascular issues in the body. Interventionalist techniques, including injecting arteries with dye, visualizing these via x-ray, and opening up blockages, developed from early pioneers' bold experiments which aimed to find safer and better ways to treat coronary artery and other atherosclerotic vascular disease. The present platform 100 provides a tool to assist the practitioner 130 in such interventionalist techniques.

Currently, the major interventional specialties are interventional (or vascular) radiology, interventional cardiology, and endovascular surgical (interventional) neuroradiology. All three are perfecting the use of stents and other procedures to keep diseased arteries open, while also evaluating the application of these procedures. The present platform 100 is believed to be applicable and valuable to all three interventional specialties.

Interventional radiologists (IR), also referenced as 130 herein, are board-certified radiologists who specialize in minimally invasive, targeted treatments. Traditionally, they use available imaging systems, from x-rays to MRIs, in order to advance a catheter in the body, usually in an artery, to treat the source of disease non-surgically. According to the Society of Interventional Radiology (SIR), "As the inventors of angioplasty and the catheter-delivered stent, IRs pioneered minimally invasive modern medicine." Interventional radiologists 130 are still considered to be at the center of the interventionalist movement. Charles Dotter is considered the father of angioplasty and interventional radiology. He is remembered as a brilliant innovator and Nobel Prize nominee who authored 300 publications and predicted much of what has eventually come to fruition in the field during the past 40 years. The platform 100 of the present invention certainly advances the work of Dr. Dotter and will be another tool for implementing procedures by Interventional radiologists 130.

According to The Society for Cardiovascular Angiography and Interventions, "Interventional cardiology is the specialized branch of cardiology that treats coronary artery disease with balloon angioplasty and stenting, therapies that unblock clogged arteries that supply blood to the heart, stop heart attacks and relieve angina, or chest pain." Interventional cardiologists (IC), 130 herein, are also trained to do procedures on cardiac valves and other structures. Whereas Dotter is the father of interventional radiology, Andreas Gruentzig, who perfected coronary angioplasty, is considered the father of interventional cardiology. He did much of his angioplasty work in the United States at Emory University, where the first controlled trial comparing angioplasty to coronary artery bypass surgery took place. His techniques allowed for visualization of the coronary arteries and better treatment of coronary artery disease. Angioplasty went through many phases in order to combat complications associated with the procedure with the most notable issue being restenosis, or renarrowing, of the coronary arteries. Another problem was, and still is, the formation of new clots. The platform 100 of the present invention builds directly on the foundation of Dr. Gruentzig and improves vascular visualization via flow based imaging, e.g. angiograms.

Interventional neuroradiology is one of the terms for neurology, neuroradiology and neurosurgery-based practices involving interventional endovascular techniques. This specialty is in the process of redefining and renaming itself, now using the terminology endovascular surgical (EVS) neuroradiology.

Vascular Mapping Tool/Interventional Therapy Assist Device

One aspect of the present invention may be described as an AI based arterial access modeling platform 100 based upon dynamic imaging, such as angiography or arteriography 110. Angiography or arteriography is a medical imaging technique used to visualize the inside, or lumen, of blood vessels and organs of the body, with particular interest in the arteries, veins, and the heart chambers. This is traditionally done by injecting a radio-opaque contrast agent into the blood vessel and imaging using X-ray based techniques such as fluoroscopy. The term angiography has been applied to radionuclide angiography and newer vascular imaging techniques such as CT angiography and MR angiography. The term angiogram is often used to refer to the test or resulting image and data performed by angiography or arteriography techniques. Though the word angiogram can describe both an arteriogram and a venogram, in everyday usage the terms angiogram and arteriogram are often used synonymously.

The present invention provides an artificial intelligence based vascular mapping and interventional procedure assisting platform 100 based upon dynamic flow based imaging, preferably angiograms 110, and biomarkers 120. The platform 100 may be a deep artificial neural network and may be accurately described as a 3D multilayer convolutional network. The platform 100, for vascular mapping, essentially reads or interprets dynamic flow based medical images or scans, namely angiograms 110. The platform 100 is trained, as described below using a number of known examples to allow the platform 100 to determine what patient vascular anatomy looks like and to allow the platform to accurately map and label the anatomy for the clinician.

The AI platform 100 of the invention is configured to identify the arteries and veins of a patient from a dynamic flow based image such as an angiogram 110 as well as identify bifurcation points and desired access point for designated interventional procedures. The AI platform 100 will locate the femoral artery 160 and the bifurcation point 170 of the femoral artery, all based upon the supplied dynamic imaging 110, such as an angiogram. The bifurcation point 170 will be identified for the clinician 130 on the platform interface or display 140. The interface may be any desired computer display system and interface such as a multi monitor computer system, standard desktop, laptop, tablet or even smartphone in some instances. Location of the bifurcation point 170 of the femoral artery 160 is critical for femoral access in interventional procedures. The femoral artery 170 is the optimal access point 180 for femoral arterial puncture. A higher or lower puncture can result in various vascular complications and by the proper definition of the femoral arterial bifurcation level 170, and the optimal puncture point 180, such complications can potentially be avoided.

The platform 100 formed by the multilayer convolutional network may be configured for segmenting data sets of flow based dynamic scans 110, generally angiograms, into resolution voxels. A voxel, generally, is one of an array of elements of volume that constitute a notional three-dimensional space, especially each of an array of discrete elements into which a representation of a three-dimensional object is divided. A voxel, in general, represents a value on a regular grid in three-dimensional space. As with pixels in a bitmap, voxels themselves do not typically have their position (their coordinates) explicitly encoded along with their values. Instead, the position of a voxel is inferred based upon its position relative to other voxels (i.e., its position in the data structure that makes up a single volumetric image). The phrase "resolution voxel" references the smallest volumetric region that the platform can segment the data from a scan into for classification, which in this case can be a cube of 1 mm per side. The data from any data set of an image is generally cropped to the region of interest (e.g., the image within the skull or within the spine), and the data segmented into the resolution voxels for processing and classification. Each resolution voxel will also have a time based component, and it should be apparent that non-occluded vascular structures will typically vary over time in the flow based scans of the present invention.

The platform 100 is trained using the same image interpretation "rules" used to train medical professionals when interpreting the dynamic scans 110, such as angiograms. These rules or guidelines are based upon in-depth cognitive knowledge of related anatomical pathophysiology, vascular anatomy and pathology, and an understanding of the full range of possibilities, and are generally known in the art to trained professionals. For example see *Angiographic Projections Made Simple: An Easy Guide to Understanding Oblique Views* CathLab Digest, Volume 19—Issue 8—August 2011; also *Assessment of Femoral Artery Bifurcation Level with Conventional Angiography* Cureus 10(10): e3479 (Oct. 22, 2018).

The critical step in the creation of a meaningful operational platform 100 is supervised learning of the platform 100 on a known dataset (sometimes called ground truth dataset or training dataset). The training dataset represents dynamic flow based images 110, namely angiograms, of patients which has the vasculature of the subjects already known, as well as the set of biomarkers 120 and with known patient outcomes. The aim of supervised, machine learning is to build a network on the platform 100 that makes predictions based on evidence in the presence of uncertainty. As the adaptive algorithms of the platform 100 identify patterns in data, the platform 100 "learns" from the observations. When exposed to more observations, the platform 100 improves its predictive performance.

The supervised learning is defined as classification, as the goal of the platform 100 is to assign a label (or class) from a finite set of classes to an observation. That is, responses of the platform 100 are categorical variables. Specifically the platform 100 is configured to classify the tissue within the "classification voxels" of a specific given data set. The classification or label in the broadest context of the invention may merely be a binary choice of "vascular tissue" or "non-vascular tissue".

The keys to the training data set used in training in the supervised learning is that the classification voxels or each scan will all be identified or labeled to provide a ground truth for the supervised learning. Typically these will be training scans provided by, or proofed by, clinicians 130 in which each classification voxel of the training set is properly identified or labeled and verified. Known labels for the training set represent the ground truth or known values that the platform 100 is training upon or towards, and the desire for the platform 100 is that the predicted labels for each classification voxel provided by the platform 100 matches known labels for each classification voxel of the training set.

In practice, the labels of the training set may only be of the classification voxels that are of interest, whereby only certain desired aspects of a scan are physically listed and the remaining areas are unnoted classification voxels. The training data set must include a statistically significant number of distinct full scans (or separate patients). At least 40 full scans is believe to provide a statistically significant training set, although greater numbers will yield better training for the platform 100. Preferably at least 60 full scans are used, and more preferably at least 100 full scans are used in training.

In the supervised learning, for each scan, or angiogram 110, the multilayer convolutional network of the platform 100 segments the data set into resolution voxels (after cropping to region of interest) and will classify each classification voxel with a detailed label (e.g. vasculature, femoral artery, distance from bifurcation, etc.) based upon the network rules of the platform 100. The predicted label for each classification voxel is compared with the ground truth label for the classification voxel provided by the verified training set and the platform 100 is modified (learns) accordingly.

Following supervised learning is validation of the platform 100 of the present invention, wherein validation of classification voxels of a specific given validation data set by the multilayer convolutional network of the platform 100 provides that each classification voxel of the validation data set has a predetermined ground truth. The validation of the platform operates similar to training or supervised learning, but for a different purpose. The validating dataset of the validation can typically be less distinct scans 110 of patients than the training data set used in the supervised learning, such as 10-20 scans. The validating dataset will also have ground truth labels for the classification voxels, but these labels are primarily used to evaluate the performance of the platform 100 rather than train the platform 100.

The validation may result in a standard measuring metric like a Dice score or Sørensen-Dice coefficient or a Hausdorff distance. The Sørensen-Dice coefficient or simply Dice Score (known by many monikers) is a statistic used to gauge the similarity of two samples and is a quotient of similarity and ranges between 0 and 1. The Sørensen-Dice coefficient was independently developed by the botanists Thorvald Sørensenand and Lee Raymond Dice, who published in 1948 and 1945 respectively. The Dice Score has been commonly used in image segmentation, in particular for comparing algorithm output against reference masks in medical applications. See Zijdenbos, A. P.; Dawant, B. M.; Margolin, R. A.; Palmer, A. C. (1994). *Morphometric analysis of white matter lesions in MR images: method and validatio*". IEEE Transactions on Medical Imaging. Institute of Electrical and Electronics Engineers (IEEE). 13 (4): 716-724. The Hausdorff distance 60 is used to measure the difference between two different representations of the same 3D object particularly when generating level of detail for efficient display of complex 3D models. See Cignoni, P.; Rocchini, C; Scopigno, R. (1998) *Metro: Measuring Error on Simplified Surfaces*. Computer Graphics Forum 17 (2): 167-174. A successful validation of the platform is a mean Dice Score greater than 0.60 or an absolute value of a mean Hausdorff distance of greater than 1.50 (log scale) or less than −1.50 (log scale).

Following validation to obtain the scores for the platform 100 on standardized measurements, the ground truth labels of the validation data set can be used to further train the platform 100 in the same manner as the supervised learning above, such that validation can further improve effectiveness of the platform 100. The supervised learning and validation can be combined effectively in one step with a final testing subset of the training dataset used for validation. The validation may, of course, be different than the training of supervised learning. Unsuccessful validation of a platform 100 can be cured with further supervised learning and or supplemental rules added to the network outside of a supplemental to the supervised learning.

Following successful validation the platform 100 is used in practice by practitioners, known as platform implementation. The clinician or technician 130 selects the desired labels (or set of labels) for the classification voxels that are the same as or less complex (more generic) than those used in validation, but generally equal in complexity to the validation labels. In other words the clinician 130 can select the desired output of the AI platform 100 of the invention.

The platform 100 can receive further learning based upon any ground truth or known feedback it receives. For example the platform 100 should be capable of receiving confirmation of, or correction of any label of any classification voxel for any data set. In accordance with the recommendations of the Radiological Society of North America (RSNA), the American College of Radiology (ACR), and The Academy for Radiology and Biomedical Imaging Research (The Academy) the platform 100 is configured and designed for stand-alone distributed training to reduce the need for data exchange between institutions, however communication between separate platforms 100 can allow for an exchange of known "ground truths" of each platform 100 in co-operative co-training (provided the separate platforms 100 utilize a uniform consistent labeling scheme). This co-training may be in the form of training updates sent to all platforms 100 in the field, based upon ground truths from a distributed collection of platforms 100 that are uploaded to a central location. The platform 100 is set up for stand-alone operation, but this co-operative improvement of the network of each platform 10 is disclosed as possible. The stand-alone aspects of the platform 100 allow the labeling rules to be specifically tweaked or set by the institution and users implementing the platform (and designing and providing the training and validating sets), however such personalization can minimize the ability to have co-operative learning across platforms 100.

The classification labels for classification voxels is preferably expanded to include desired vascular details. The platform 100 may utilize any existing or known segmentation regimes within its classification of voxels. For example, the internal carotid artery (ICA) has been repeatedly subdivided into discrete parts, or segments, to aid description of its pathology. The first classification was devised by Fischer in 1938, designating intracranial ICA from C1-C5, against direction of blood flow. In 1981, Gibo, Lenkey, and Rhoton, established a segmentation of the ICA which became a landmark in vascular neurosurgery, and they classified their findings according the the Gibo system, which numbered 4 segments, cervical, petrous, cavernous, and supraclinoid, with an alphanumeric designation of C1 thru C4, in direction of blood flow. The landmark present-day ICA segmentation classification, however, belongs to Bouthillier and colleagues, who proposed a "Modified Fischer Classification" in 1996, with alphanumeric designation of ICA segments in direction of blood flow. The present platform can implement any desired known segmentation system provided the rules for such segmentation system are definitive and generally objective. The AI platform 100 is actually quite robust at implementing even a subjective standard when used with a sufficient training dataset, which represents one of the advantages of AI systems.

Additionally, the platform 100 will, in a preferred embodiment, specifically identify the Femoral artery (160) from the dynamic images 110 (namely angiograms) including the Size (at least an identification of greater than or less than 4 mm diameter), and the Location related to bifurcation (above or below). The bifurcation location 170 and optimal access location 180 will also be identified. The platform 100 of the preferred embodiment can identify Carotid artery 190 (neck) with a Right or left designation and further identify at least the presence of Narrowing (yes or no). The platform 100 of the preferred embodiment will identify what degree narrowing and/or whether such narrowing is acceptable such that it is within tolerable range. The platform 100 of the preferred embodiment will similarly identify the Internal carotid artery 200, including a Right or left designation and the presence of a perceived Abnormality in the internal carotid artery based upon the angiogram images 110. The platform 100 of the preferred embodiment will also identify the Vertebral artery 210, including Right or left dominance (right, left, co-dominant), and any perceived abnormality. The AI platform 100 will identify and automate dimension of the arteries and veins to the extent possible. Again the AI platform 100 will locate the major arteries and their bifurcation points for interventional access.

Closure Device Indication

There are a large number of commercially available closure devices available for interventional procedures. As a small sample consider the following: The MYNXGRIP® Vascular Closure Device achieves secure extravascular closure by utilizing the GRIP™ sealant which actively adheres to an artery or vein. The AngioSeal vascular closure device seals femoral artery punctures and creates a mechanical seal by sandwiching the arteriotomy between a bioabsorbable anchor and collagen sponge. The Cardiva Boomerang Wire vascular closure device is a manual compression assist device. The ExoSeal Vascular Closure Device uses a bioabsorbable PGA-plug (Polyglycolic Acid) to close the femoral artery puncture site. The FastSeal Bioabsorbable Vascular Access Closure System uses bioabsorbable components in a compression seal structure for closing vascular access sites. The Mynx Vascular Closure Device is an extravascular sealing device designed to facilitate hemostasis without sutures or implants.

With the large variety of choices for closures available, it is difficult for the clinicians 130 planning an interventional procedure for a patient to even know about all the options generally as opposed with which closure devices may be appropriate or contraindicated for a particular procedure and or a particular patient. There are tools to assist in the dissemination of information on this point such as Which Medical Device which is a review and information website (www.whichmedicaldevice.com) about medical devices developed "by clinicians for clinicians". This website was launched with the aim of sharing information about medical devices to help clinicians make better decisions and use devices well.

It is obvious that using a closure device that subsequently fails can lead to detrimental patient outcomes. However subsequent closure failure is not the only detrimental effect of sub-optimal closure selection. More commonly a clinician 130 can waste significant time in a procedure setting up to use a closure that is inappropriate due to patient physiology, access point or size, before moving to an alternative closure system or technique that is usable. Understanding and evaluating suitable or unsuitable closure systems based upon specific patient physiology, and procedures prior to a procedure can greatly assist the interventional procedure and ultimately patient outcomes. The platform 100 of the present invention is coupled to a closure device library 220 having a complete listing of available closures as well as appropriate indications of use and contra-indications of use. One sometimes overlooked contraindication is the actual availability of a given closure (i.e. is it carried by the facility and in stock at the moment), and thus availability will be a meaningful part of the library 220.

The platform 100 of the present invention incorporates the patient physiology, based upon the angiogram and other available patient information, together with the library 220 to designate which closure devices would be appropriate and/or more significantly which closure devices would be contra-indicated based upon the procedure, the designated access and the patient physiology. The goal of the platform 100 is also to help clinicians make better decisions and use devices well and save operation time and improve patient outcome by preventing use of, or the attempted use of, closures that are inappropriate.

The platform 100 of the present invention will express stenosis in the femoral and carotid artery according to NASCET (North American Symptomatic Carotid Endarterectomy Trial) criteria based upon the patient angiograms 110. For details of distinct criteria or categorization methods see *Equivalence of measurements of carotid stenosis. A comparison of three methods on* 1001 *angiograms. European Carotid Surgery Trialists' Collaborative Group* Stroke 25:2435-2439 (1994); and *How to measure carotid stenosis* Radiology Vol. 186, No. 2 (February 1993). The platform 100 of the present invention may categorize the measured Degree of stenosis was categorized into mild (<50%), moderate (50% to 69%), or severe (70% to 99%) concordant with NASCET guidelines. This designation of the platform 100 illustrates a major advantage of using dynamic imaging such as angiograms as opposed to static CT images, in that the platform 100 essentially uses a broader range of physiological insights.

Biomarkers 120

The platform 100 of the invention uses patient biomarkers 120 for assisting interventional cardiologists 130. As background, brain injury resulting from stroke is a leading cause of morbidity in the USA and despite significant efforts the development of neuro-protectants against stroke has largely failed. The only efficacious treatment for ischaemic stroke is revascularization using clot-busting agents such as tissue plasminogen activator (tPA), or endovascular mechanical thrombectomy for patients with proximal large vessel occlusions. Haemorrhagic stroke represents a subset of stroke cases (~15%), yet can greatly confound stroke care as it is an absolute contraindication for the administration of chemical thrombolytics.

The time required for diagnosis, triage and workup often results in delay in the administration of tPA, or missing the therapeutic window of an efficacious treatment altogether. While medical imaging remains the gold-standard for stroke diagnosis and management and these modalities are largely accurate and effective; currently there remain inherent limitations of these techniques as currently implemented around interpretation, challenges to imaging certain brain regions (e.g. cerebellum and brainstem). It has been theorized that a blood-based biomarker 120 that could rapidly discriminate between stroke subtypes would be clinically valuable, and open the future development of a point-of-care (POC) tool, broadening access to effective therapeutics. The present invention incorporates the use of such blood based biomarkers 120 into the results of the system where the blood tests are available to the platform 100.

It has been recognized that RNAs were contained within and could be shuttled between cells in extracellular vesicles, such as exosomes *Detection of microRNA expression in human peripheral blood microvesicles* PLoS One. 2008; 3(11):e3694. Extracellular RNAs (ex-RNAs) are typically carried within vesicles or associated with RNA-binding proteins or lipoproteins, see *Circulating microRNAs: potential and emerging biomarkers for diagnosis of cardiovascular and cerebrovascular diseases* Biomed Res Int. 2015; 2015:730535. After discovery of RNA within extracellular vesicles, the detection and expression of these circulating RNA species were correlated with different disease subtypes as well as disease progression. See *Circulating microRNA signatures of tumor-derived exosomes for early diagnosis of non-small-cell lung cancer*, Clin Lung Cancer. 2009; 10(1): 8-9; *Glioblastoma microvesicles transport RNA and proteins that promote tumour growth and provide diagnostic biomarkers*, Nat Cell Biol. 2008; 10(12):1470-1476; and *Exosome-derived miRNAs and ovarian carcinoma progression*, Carcinogenesis. 2014; 35(9):2113-2120. These ex-RNAs can be taken up by cells, functionally regulate cellular processes and impact tissue microenvironments. The detection of miRNAs in circulation has been associated with a host of central nervous system diseases including neurogenerative diseases and brain cancer, making them attractive biomarkers for inaccessible tissues and disease regions, see *MicroRNAs as biomarkers for CNS cancer and other disorders*, Brain Res. 2010; 1338:100-111.

The abundance and stability of circulating miRNAs, due to inherent structure and packaging within vesicles, makes them even more ideal candidates for biomarkers 120 serve as potential biomarkers that allow for differentiation between major stroke subtypes; intraparenchymal haemorrhage (IPH), subarachnoid haemorrhage (SAH) and ischaemic stroke. See *Circulating microRNAs as biomarkers for acute ischemic stroke: a systematic review*, J Stroke Cerebrovasc Dis. 2018; 27(3):522-530; *MicroRNAs as diagnostic and prognostic biomarkers in ischemic Stroke-A comprehensive review and bioinformatic analysis*, Cells. 2018; 7(12):249; *Using extracellular circulating microRNAs to classify the etiological subtypes of ischemic stroke* Transl Stroke Res. 2018; 10(4):352-361; *Comparison of miR-124-3p and miR-16 for early diagnosis of hemorrhagic and ischemic stroke*, Clin Chim Acta. 2014; 433:139-144; *Brain and blood microRNA expression profiling of ischemic stroke, intracerebral hemorrhage, and kainate seizures*, J Cereb Blood Flow Metab. 2010; 30(1):92-101. Some more definitive and useful work is presented in *Extracellular microR-*

*NAs in blood differentiate between ischaemic and haemorrhagic stroke subtypes* J Extracell Vesicles. 2020; 9(1): 1713540.

The platform 100 of the present invention utilizes these biomarkers 120 for stroke differentiation and combines this with the image analysis. The combination yields synergistic results in patient diagnostic and overall improvements patient care and outcomes.

Pandemic/Healthcare System Stresses

Since the start of COVID, health care system in the United States have seen total stroke volume decrease, increased strokes in younger patients, more patients presenting with complicated or atypical strokes, and fewer neurologists available for helping to triage these patients. The complicated presentations and the reduced numbers of providers in more remote facilities has challenged healthcare systems ability to maintain delivery of optimal care to patients. The platform 100 of the present invention, if properly implemented can help to triage these patients remotely with maintained communication across the entire care team (130 collectively) and can assist in providing optimal patient care through this, or similar, health crisis, and do so cost effectively. Patient safety and resource management is of utmost importance during a pandemic.

Reducing futile transfers and ensuring that only patients with large vessel occlusions that will benefit from mechanical thrombectomy are transferred to larger or hub centers is helpful in this scenario. Minimizing futile transfers decreases the risk of exposure for patients transferred to hub hospitals that typically have more COVID patients and helps to reserve limited resources and ICU beds for COVID patients at the hub. When patients who are unlikely to benefit from mechanical thrombectomy are retained in the more remote smaller facilities the patient can be better managed remotely (out of the hub) medically in the same manner they would be cared for at the comprehensive center. Conversely, patients with large vessel occlusions that can benefit from thrombectomy which are costly for some smaller hospitals when they are not transferred. These patients often have large infarcts driving long lengths of stay both in the ICU and in the hospital. These outcomes are not only suboptimal for the patient but costly for the smaller hospital, as the costs associated with care often exceed the associated payments received for the services provided. The platform 100 of the present invention can cost-effectively optimize stroke triage during COVID, or similar healthcare stresses, across a large hub and smaller associate networks, helping to pull only the patients that are likely to benefit from mechanical thrombectomy to the comprehensive center.

CONCLUSION

The present invention provides effective and efficient precision artificial intelligence based vascular mapping and interventional procedure assisting platform 100 based upon dynamic flow based imaging 110 and further including biomarkers, namely blood based biomarkers 120.

In one aspect the invention yields a post-stroke management tool in which an angiogram 110 and conventional bloodwork (with biomarkers 120) can be inputted into the AI platform 100 and the clinician 130 is presented in real time with classification of the stroke; and if interventional procedure (e.g., an interventional thombectomy) is indicated then vascular mapping is provided with bifurcation points and the desired access 180 illustrated together with a listing of accepted or counter indicated closure systems that may be used.

In one analogous aspect or implementation the invention yields a pre-stroke management tool in which an angiogram 110 and conventional bloodwork (with biomarkers 120) can be inputted into the AI platform 100 and the clinician 130 is presented in real time with stroke prediction and if interventional procedure is indicated (e.g. interventional angioplasty) then vascular mapping is provided with bifurcation points and the desired access 180 illustrated together with a listing of accepted or counter indicated closure systems that may be used.

The AI platform 110 of the present invention may not be integrated and may only have certain subcomponents, like only vascular mapping, or closure review or biomarker implementation, but again there is believed to be synergistic advantages with the combinations of these tools.

The platform 100 is not limited to stroke treatment and prevention, although this is certainly the most significant application, namely as a stroke assessment and management tool. Additionally the platform 100 is designed using dynamic imaging 120, such as angiograms, but is not intended to be limited to only angiograms. The platform 100 according to the principles of the present invention can be implemented using other dynamic imaging scans and further can be supplemented with static scans for a given patient.

It will be apparent to those of ordinary skill in the art that various modifications may be made to the present invention without departing from the spirit and scope thereof. The scope of the present invention should be defined by the appended claims and equivalents thereto.

What is claimed is:

1. An artificial intelligence based vascular mapping and interventional procedure assisting platform configured to identify at least the femoral artery and the bifurcation point of the femoral artery of a patient based upon dynamic imaging of the patient, wherein the platform is configured to identify and automate dimension of the arteries and veins of the patient and will locate and display the major arteries and their bifurcation points for interventional access, and wherein the platform is configured to identify on a display for the clinician an optimal access location on the patient for performing interventional procedures on the patient.

2. The artificial intelligence based vascular mapping and interventional procedure assisting platform according to claim 1, wherein the platform is configured to identify the Carotid artery with a right or left designation and further identify at least the presence of narrowing.

3. The artificial intelligence based vascular mapping and interventional procedure assisting platform according to claim 2, wherein the platform is configured to identify what degree of narrowing and whether such narrowing is acceptable.

4. The artificial intelligence based vascular mapping and interventional procedure assisting platform according to claim 3, wherein the platform is configured to identify the internal carotid artery, including a right or left designation and the presence of a perceived abnormality in the internal carotid artery.

5. The artificial intelligence based vascular mapping and interventional procedure assisting platform according to claim 3, wherein the platform is configured to identify the vertebral artery, including right or left dominance and any perceived abnormality.

6. The artificial intelligence based vascular mapping and interventional procedure assisting platform according to claim 1, wherein the platform uses patient biomarkers.

7. The artificial intelligence based vascular mapping and interventional procedure assisting platform according to claim 6, wherein the patient biomarkers are blood-based biomarker and wherein the platform uses these to discriminate between stroke subtypes.

8. The artificial intelligence based vascular mapping and interventional procedure assisting platform according to claim 1, wherein the platform is coupled to a closure device library having a complete listing of available closures as well as appropriate indications of use and contra-indications of use.

9. The artificial intelligence based vascular mapping and interventional procedure assisting platform according to claim 8, wherein the platform incorporates the patient physiology together with the library to designate which closure devices would be appropriate and which closure devices would be contra-indicated.

10. An artificial intelligence based vascular mapping and interventional procedure assisting platform wherein the platform is coupled to a closure device library having a complete listing of available closures as well as appropriate indications of use and contra-indications of use and wherein the platform incorporates the patient physiology based upon dynamic imaging of the patient together with the library to designate which closure devices would be appropriate and which closure devices would be contra-indicated and further wherein the platform is configured to identify the femoral artery and the bifurcation point of the femoral artery of a patient and is configured to identify on a display for the clinician an optimal access location on the patient for performing interventional procedures on the patient.

11. The artificial intelligence based vascular mapping and interventional procedure assisting platform according to claim 10, wherein the platform uses patient biomarkers.

12. The artificial intelligence based vascular mapping and interventional procedure assisting platform according to claim 11, wherein the patient biomarkers are blood-based biomarker and wherein the platform uses these to discriminate between stroke subtypes.

13. An artificial intelligence based vascular mapping and interventional procedure assisting platform wherein the platform is a stroke management tool in which an angiogram and conventional bloodwork can be inputted into the platform and the platform provides a classification of a stroke and stroke prediction; and whether an interventional procedure is indicated, and wherein if interventional procedure is indicated then vascular mapping is provided with bifurcation points and the desired access illustrated together with a listing of accepted or counter indicated closure systems that may be used, wherein the desired access is illustrated by having the platform identify the femoral artery and the bifurcation point of the femoral artery of a patient and identify on a display for the clinician an optimal access location on the patient for performing interventional procedures on the patient, and wherein the platform incorporates the patient physiology together with the library to designate which closure devices would be appropriate and which closure devices would be contra-indicated.

14. The artificial intelligence based vascular mapping and interventional procedure assisting platform according to claim 13, wherein the platform is configured to identify and automate dimension of the arteries and veins and will locate the major arteries and their bifurcation points for interventional access.

* * * * *